(12) United States Patent
Lee et al.

(10) Patent No.: US 7,435,811 B2
(45) Date of Patent: Oct. 14, 2008

(54) METHOD FOR PREFERENTIALLY REMOVING PROTEIN OVER NUCLEIC ACIDS USING PHYSICAL AS WELL AS CHEMICAL MEANS OF REMOVAL OF THE PROTEIN

(75) Inventors: Myo-yong Lee, Suwon-si (KR); Ki-woong Han, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/396,761

(22) Filed: Apr. 3, 2006

(65) Prior Publication Data

US 2006/0223100 A1    Oct. 5, 2006

(30) Foreign Application Priority Data

May 4, 2005    (KR) .................. 10-2005-0037427

(51) Int. Cl.
*C07H 21/00* (2006.01)
(52) U.S. Cl. .................................... 536/25.4
(58) Field of Classification Search ............... None
See application file for complete search history.

(56) References Cited

U.S. PATENT DOCUMENTS 6,875,617 B2 *   4/2005   Alam ............... 436/86
6,921,537 B2 *   7/2005   Zlotnick ........... 424/234.1

OTHER PUBLICATIONS

Alan D. Antoine, Chairperson, Department of Biochemistry and Microbiology, Rutgers University, 76 Lipman Drive, New Brunswick, New Protein Purification: Precipitation, course numbers 115:412/508, Proteins and Enzymes, spring 2004, also found at: www.cook.rutgers.edu/~dbm/precipitations04.pdf.*
Hengen, Methods and reagents—Optimizing multiplex and LAoPCR with betaine, TIBS 22—Jun. 1997, pp. 225-226.*
Schneider, W. C., "Phosphorus Compounds In Animal Tissues," *J. Biol. Chem.* (1945) 161: 293-303.
Sivaraman, T. et al., "The Mechanism of 2,2,2-Trichloroacetic Acid-Induced Protein Precipitation," *Journal of Protein Chemistry* (1997) 16(4): 291-297.

* cited by examiner

*Primary Examiner*—Kenneth R. Horlick
*Assistant Examiner*—Mark Staples
(74) *Attorney, Agent, or Firm*—Cantor Colburn LLP

(57) ABSTRACT

Provided is a method of removing protein while not removing nucleic acids from a biological sample containing protein, the method including: adding a compound of formula I below and a protein nucleating agent to the biological sample containing protein:

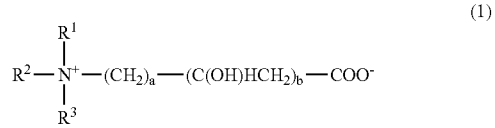

(1)

where at least two of $R^1$, $R^2$, and $R^3$ substituents are substituted or unsubstituted C1-C6 alkyl groups and the other substituent is a hydrogen atom or a substituted or unsubstituted C1-C6 alkyl group, a is an integer of 1 to 6, and b is 0 or 1, wherein b is 0 when a is not 1; treating the resultant mixture with a hydrophobic surface material in order to obtain a protein-free mixture; and separating the protein-free mixture from the hydrophobic surface material to which the protein is bound. By using the method, the protein can be selectively, effectively removed from the biological sample containing the protein while a nucleic acid is maintained in the sample.

10 Claims, 6 Drawing Sheets

METHOD FOR PREFERENTIALLY REMOVING PROTEIN OVER NUCLEIC ACIDS USING PHYSICAL AS WELL AS CHEMICAL MEANS OF REMOVAL OF THE PROTEIN

CROSS-REFERENCE TO RELATED PATENT APPLICATIONS

This application claims the benefit of Korean Patent Application No. 10-2005-0037427, filed on May 4, 2005, in the Korean Intellectual Property Office, the disclosure of which is incorporated herein in its entirety by reference.

BACKGROUND OF THE INVENTION

1. Field of the Invention

The present invention relates to a method of selectively removing a protein from a biological sample using chemicals.

2. Description of the Related Art

Efficient extraction of DNA from cells is required in many applications and is essential in molecular diagnosis, in particular, the identification and quantification of pathogenic bacteria. Molecular diagnosis is generally performed by DNA amplification after DNA extraction. Types of DNA amplification include a polymerase chain reaction (PCR), a ligase chain reaction, a stranded-displacement amplification, a nucleic acid-based amplification, a repair chain reaction, a helicase chain reaction, a QB replicase amplification, and a ligation activated transcription.

The production of high purity double-strand plasmid DNAs, single-strand phage DNAs, chromosomal DNAs, and agarose gel-purified DNA fragments is very important in molecular biology. Ideal methods of purifying DNAs should be simple, be performed rapidly and include little additional manipulation of samples. The DNAs obtained using such methods are ready for direct transformation, restriction enzyme analysis, ligation, or sequencing. Such methods are commonly used in automated production of DNA samples, which is favored in research and diagnosis labs. Generally, the preparation of plasmid DNAs from crude alcohol precipitates is laborious. Plasmid DNAs are often produced using a CsCl gradient, gel filtration, ion exchange chromatography, RNAase, proteinase K, and repeated alcohol precipitation. These methods require considerable downstream sample preparation to remove CsCl and other salts, EtBr, and alcohol, etc. Further, small negatively charged cellular components can be precipitated together with DNAs. Thus, the DNAs may be contaminated to an undesirable degree.

In general, protein largely occupies a large part of a cell composition. Accordingly, in order to purify nucleic acids from biological samples, protein that largely forms a cell should be efficiently removed. It is known that trichloroacetic acid (TCA) can precipitate protein by three chloro groups contained therein (*J. Prot. Chem.* 1997, 16(4): 291-297.) However, precipitating agents that precipitate protein or nucleating agents that nucleate protein also precipitate nucleic acids, in addition to protein. For example, it is known that genome DNAs are precipitated by TCA (*J. Biol. Chem.* 1945, 161:293-303.) Accordingly, there is a need to develop a method capable of removing only protein while not removing nucleic acids from a biological sample containing protein. Inventors of the present invention researched a method of removing protein, based on conventional techniques, and found that when a protein nucleating agent is added to a sample together with a specific compound, such as betaine, and the resultant mixture is treated with a hydrophobic surface material, protein can be efficiently removed while a nucleic acid exists in the sample.

SUMMARY OF THE INVENTION

The present invention provides a method of selectively removing protein from a biological sample using chemicals.

According to an aspect of the present invention, there is provided a method of removing protein while not removing nucleic acids from a biological sample containing protein, the method including:

adding a compound of formula I below and a protein nucleating agent to the biological sample containing protein:

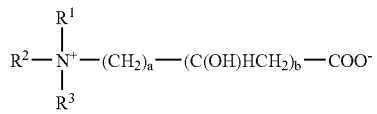

(1)

where at least two of $R^1$, $R^2$, and $R^3$ substituents are substituted or unsubstituted C1-C6 alkyl groups and the other substituent is a hydrogen atom or a substituted or unsubstituted C1-C6 alkyl group, a is an integer of 1 to 6, and b is 0 or 1, wherein b is 0 when a is not 1;

treating a resultant mixture with a hydrophobic surface material in order to obtain a protein-free mixture; and separating the protein-free mixture from the hydrophobic surface material to which the protein is bound.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
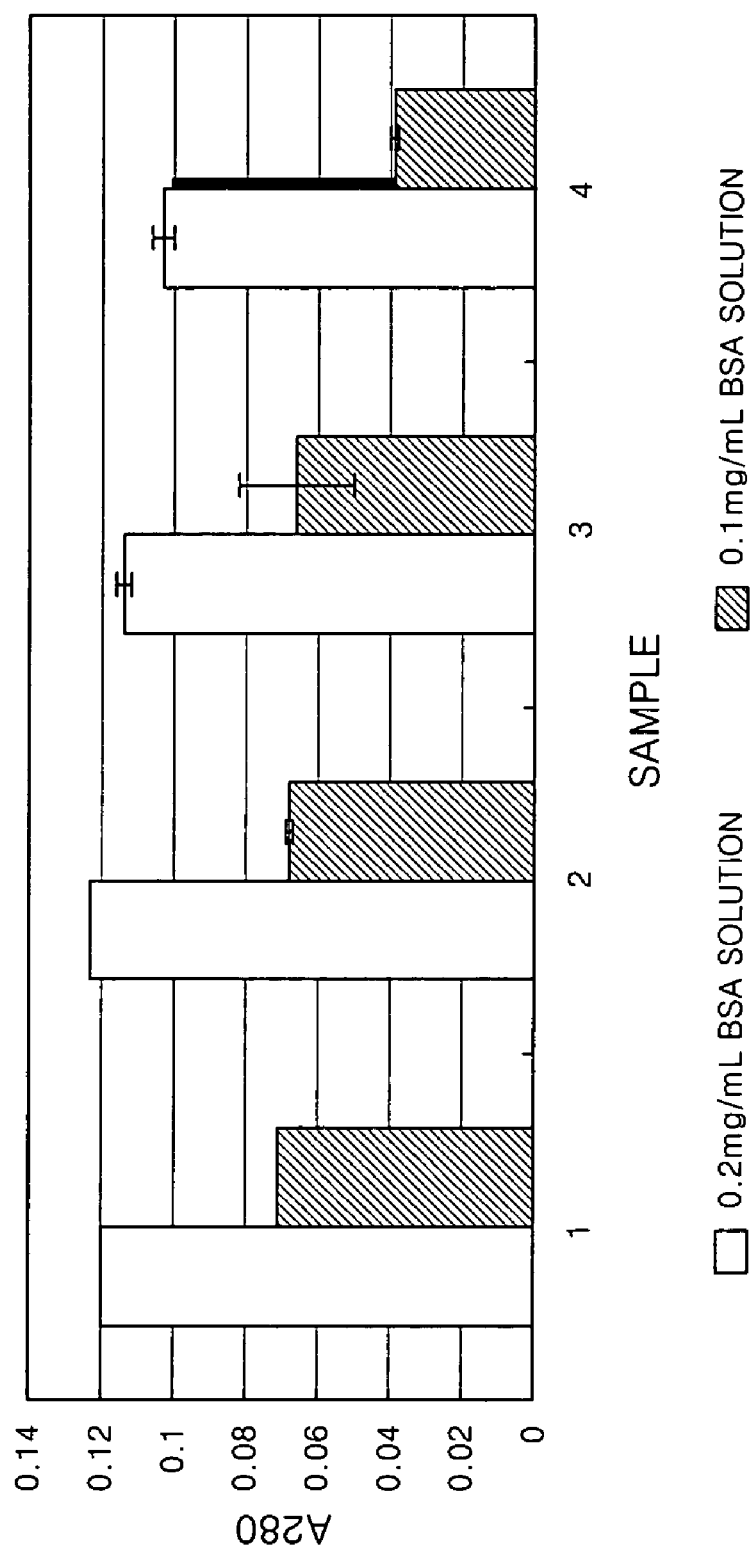
FIG. 1 is a graph of $A_{280}$ of each sample.

Hereinafter, the present invention is described in detail with reference to attached drawings.

A method according to an embodiment of the present invention includes adding a compound of formula I and a protein-nucleating agent to a biological sample containing protein. In general, precipitating agents that precipitate protein or nucleating agents that nucleate protein also precipitate nucleic acids, in addition to protein. However, such a problem can be solved by use of the compound of formula 1.

An alkyl group used in an embodiment of the present invention can be a linear or branched C1-C20 alkyl radical, preferably a linear or branched C1-C12 alkyl radical, more preferably a C1-C6 alkyl radical, and most preferably a C1-C3 alkyl radical. Examples of the alkyl group include methyl, ethyl, n-propyl, isopropyl, n-butyl, isobutyl, sec-butyl, t-butyl, pentyl, iso-amyl, hexyl, and the like.

The compound of formula I may be betaine, D-carnitine, N,N-dimethylglycine, or the like. The structures of these compounds are illustrated below:

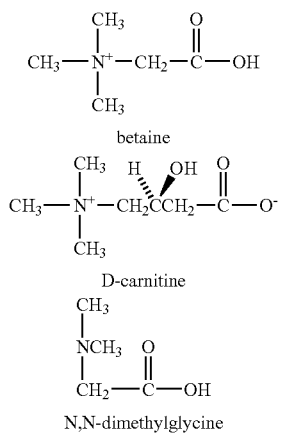

Examples of a compound having a structure similar to the compound of formula I include sarcosine represented by:

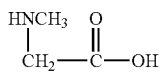

However, in Example 7, which will be described later, sarcosine is not suitable for achieving the objective of the present invention because an amine contained in the sarcosine has only one methyl group. Accordingly, a compound of formula I suitable for the present invention should have an amine group having at least two alkyl groups.

Betaine interacts with preferentially AT of a major groove of a nucleic acid. Although the exact mechanism is not known, when a protein nucleating agent and betaine are added to a biological sample containing protein to nucleate the protein, the protein nucleates and a nucleic acid remains in a supernatant. A protein nucleating agent does not fully precipitate protein and clumps several protein molecules together. In order to nucleate protein, the concentration of a protein precipitating agent should be lower than that required to precipitate protein.

The method of selectively removing protein according to an embodiment of the present invention also includes treating the resultant mixture with a hydrophobic surface material. When the mixture of the biological sample with the compound of formula I and the protein nucleating agent is treated with the hydrophobic surface material, the nucleated protein is bound to the hydrophobic surface material and the nucleic acid remains in the solution. As a result, by using the compound of formula I, only protein can be selectively removed from the biological sample containing protein.

The method of selectively removing protein according to an embodiment of the present invention also includes separating the protein-free mixture from the hydrophobic surface material to which the protein is bound. Since the protein in the cell lysate is bound to the hydrophobic surface material, the protein can be removed from the cell lysate while the nucleic acid remains therein. The protein-free sample can be efficiently used in a subsequent process, such as a polymerase chain reaction (PCR) process.

The concentration of betaine may be in the range of 0.15M to 2M. When the concentration of betaine is outside this range, the nucleic acid may precipitate or less protein can be removed.

The protein nucleating agent may contain an ionic solvent, such as trichloroacetic acid (TCA), ammonium sulfate, acetone, ethanol, or the like. The protein nucleating agent does not fully precipitate protein and clumps several protein molecules together. In the current embodiment of the present invention, the concentration of the protein nucleating agent does not need to be high because nucleation of protein, not precipitation of protein, is sufficient to bind the protein to the hydrophobic surface material after the nucleated protein is treated with the hydrophobic surface material. When the concentration of the protein nucleating agent is high, problems may arise in a subsequent process after the protein is removed. As a result, a protein nucleating agent having a low concentration is desired. For example, the concentration of the protein nucleating agent may be in the range of 0.5% to 5%. When the concentration of the trichloroacetic acid is less than 0.5%, the protein does not nucleate. On the other hand, when the concentration of the trichloroacetic acid is greater than 5%, problems may arise in a subsequent process.

The hydrophobic surface material can be a solid support having a hydrophobic surface obtained by, for example, coating a hydrophobic material on the solid support. The solid support can be a bead, a slide glass, a silicon wafer, a membrane, a metal plate, or the like. When a cell containing protein lyses, most of the protein of the cell denatures. At this time, a hydrophobic core, that is, a group of hydrophobic amino acids of the protein moves out to the surface of the cell and is exposed. Accordingly, the denatured protein can be more easily bound to a hydrophobic surface material than a hydrophilic surface material. Therefore, a material having a hydrophobic surface can be used in embodiments of the present invention without any limitation.

The removing of the hydrophobic surface material to which the protein is bound can be performed using one of a centrifugal method, a filtering method, and a magnetizing method. In order to efficiently purify a nucleic acid from a biological sample, a hydrophobic surface material to which protein is bound should be removed. Such a hydrophobic surface material to which protein is bound can be removed by centrifugation, filtration, magnetism, or the like. Filtration is suitable for realizing a lab-on-a-chip. That is, the hydrophobic surface material to which the protein is bound can be simply removed using a membrane filter so that the resultant protein-free cell lysate can be used in a subsequent process. In addition, by coating the hydrophobic material on the wall of a microchannel of a lab-on-a-chip, the protein contained in a sample is bound to the wall of the channel but a nucleic acid passes through the microchannel to join the subsequent process, when the sample flows through the microchannel. In the method of selectively removing protein according to the present embodiment, protein can be removed when the solution containing the protein is in a static state, and alternatively, protein can be removed when the solution containing the protein is in a flowing state. Particularly, when the hydrophobic surface material is coated on the wall of the microchannel and a solution containing protein is passed through the coated microchannel, the protein is bound to the wall of the microchannel but a nucleic acid passes through the microchannel when the solution containing protein passes. Therefore, this filtering method can be effectively used to purify a nucleic acid.

The present invention will be described in further detail with reference to the following examples. These examples are for illustrative purposes only and are not intended to limit the scope of the present invention.

EXAMPLE 1

Removal of Protein Using Polystyrene Beads

In order to determine whether polystyrene beads having hydrophobic surfaces efficiently remove protein, non-denatured bovine serum albumin (BSA) and denatured BSA were used as protein. The average particle diameter of the polystyrene beads was 4 μm. BSA solutions having concentrations of 0.2 g/ml and 0.1 g/ml were used, and denaturation of the BSA solutions was performed by boiling for 5 minutes. First, the polystyrene beads ($2\times10^7$ particles) were placed into an Eppendorf tube, and then 90 μl of each of the BSA solutions was added thereto and reacted at room temperature for 5 minutes. Subsequently, a supernatant was taken and the absorbance ($A_{280}$) thereof was measured at a wavelength of 280 nm. FIG. 1 is a graph of $A_{280}$ of each sample. Sample 1 was used as a BSA control and prepared using a non-denatured BSA without polystyrene beads. Sample 2 was prepared using a denatured BSA without polystyrene beads. Sample 3 was prepared using a non-denatured BSA and polystyrene beads. Sample 4 was prepared using a denatured BSA and polystyrene beads.

Referring to FIG. 1, for the BSA solution having the concentration of 0.2 mg/ml, the amount of the polystyrene beads used was so relatively small that the removed amounts of proteins contained in Samples 1 through 4 was not effectively shown. However, for the BSA solution having the concentration of 0.1 mg/ml, a greater amount of protein was removed from a supernatant when the polystyrene beads were used (Sample 4) than when the polystyrene beads were not used (Sample 2). Such results indicate that a large amount of denatured protein was bound to the polystyrene beads, and in other words, that polystyrene beads play an important role in removing protein.

EXAMPLE 2

Removal of Protein Using TCA and Polystyrene Beads

Figure 2:
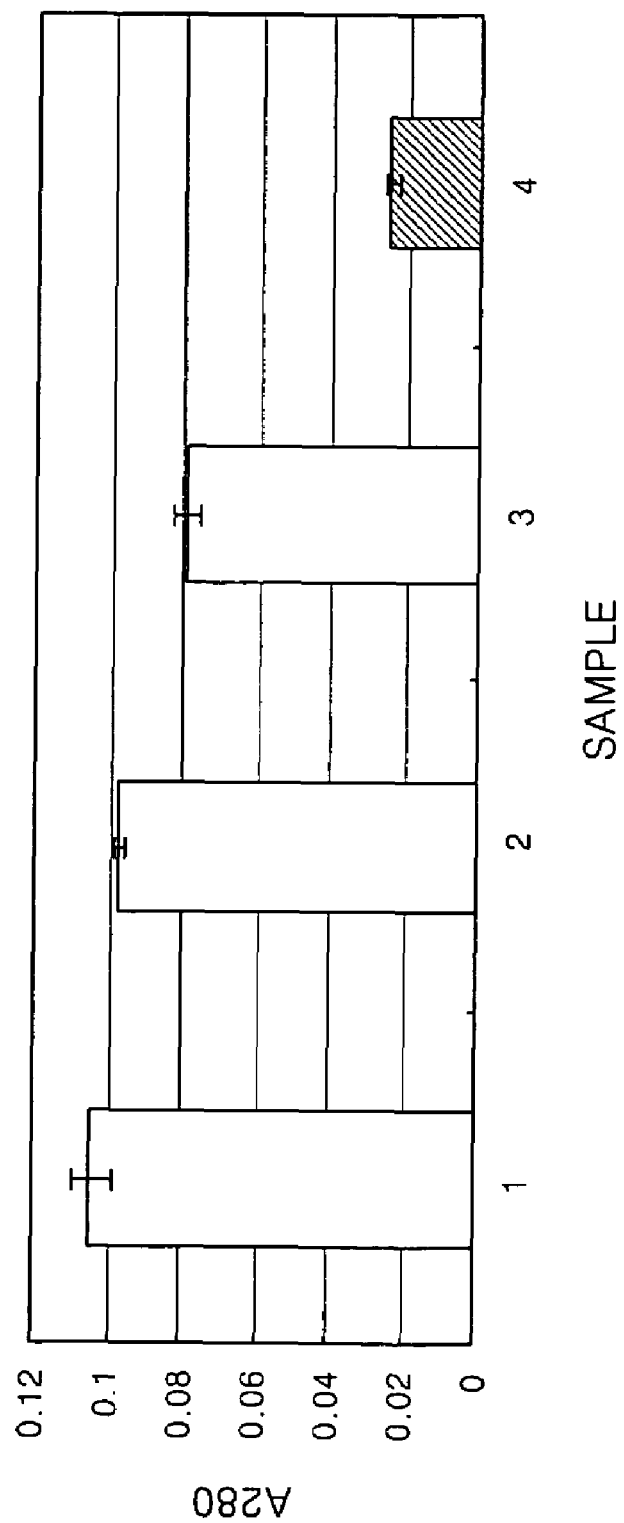
FIG. 2 is a graph of $A_{280}$ of each sample.

In order to determine whether polystyrene beads having hydrophobic surfaces and TCA efficiently remove protein, denatured BSA was used as an example. The average particle diameter of the polystyrene beads used was 4 μm, and the concentration of TCA used was 0.8%. A 0.1 mg/ml concentration of BSA solution was used, and denaturation of BSA was performed by boiling for 5 minutes. First, the polystyrene beads ($2\times10^7$ particles) were placed into an Eppendorf tube, and then 99 μl of the BSA solution was added to the tube, and TCA was added such that the final concentration of the TCA was 0.8%. The resultant mixture was reacted at room temperature for 5 minutes. Subsequently, a supernatant was taken and the absorbance ($A_{280}$) thereof was measured at a wavelength of 280 nm. FIG. 2 is a graph of $A_{280}$ of each sample. In the present experiment, all of the BSA used was denatured BSA. Sample 1 was used as a BSA control and prepared without polystyrene beads and TCA. Sample 2 was prepared using TCA but without polystyrene beads. Sample 3 was prepared using polystyrene beads but without TCA. Sample 4 was prepared using TCA and polystyrene beads together.

Referring to FIG. 2, when only TCA was used (Sample 2), less protein was removed; when only polystyrene beads were used (Sample 3), more protein was removed than when only TCA was used; and when polystyrene beads and TCA were used together (Sample 4), the protein contained in the supernatant was almost completely removed.

Accordingly, it was found that by using the method of selectively removing protein according to the embodiment of the present invention, the protein contained in a supernatant of a cell lysate could be almost completely removed.

EXAMPLE 3

Inhibition Effect of Betaine on Nucleic Acid Precipitation

In order to determine whether betaine inhibits precipitation of a nucleic acid, that is whether betaine retains the nucleic acid in a supernatant, an *E. coli* genome DNA was used and the average particle diameter of polystyrene beads used was 4 μm. 0.8% TCA, 25 ng/μl of *E. coli* genome DNA, and 0M, 0.5M or 1M betaine solution were used in the present experiment. First, *E. coli* genome DNA was added to each of the betaine solutions so that the final concentration of *E. coli* genome DNA was 25 ng/μl. 99 μl of each of the resulting solutions was added to an Eppendorf tube. Next, $2\times10^7$ particles of polystyrene beads were added to the tube. Then, TCA was added to the tube such that the final concentration of TCA was 0.8%. This mixture was reacted at room temperature for 5 minutes. Subsequently, the reaction product was neutralized by adding 10×PBS (produced by Invitrogen, USA) to the mixture until the final concentration of PBS was 1×PBS. Then, the neutralized product was centrifuged at 5000×g for 5 minutes to precipitate polystyrene beads, and then a supernatant thereof was obtained. The absorbance ($A_{260}$) of the supernatant was measured at a wavelength of 260 nm. Table 1 shows a relative amount of the *E. coli* genome DNA contained in the supernatant.

TABLE 1

|  | 0M betaine | 0.5M betaine | 1M betaine |
| --- | --- | --- | --- |
| Control | 100% | 100% | 100% |
| TCA | 0% | 68.7% | 76.2% |
| TCA-Bead | 0% | 61.6% | 74.1% |

As shown in Table 1, when betaine was not added and only TCA was added, and when betaine was not added and TCA and polystyrene beads were added, DNA precipitated and thus DNA did not exist in the supernatant. That is, although TCA efficiently removed protein, the TCA also precipitated DNA contained in the supernatant. However, when betaine was added together, only a small amount of DNA precipitated and about 60%-70% of DNA existed in the supernatant. That is, by adding betaine, DNA contained in the supernatant did not precipitate while TCA precipitated protein, and thus DNA could exist in the supernatant under the protection of betaine.

EXAMPLE 4

Confirmation of Precipitation of Nucleic Acid By TCA using PCR Amplification Precipitation of the entire *E. coli* genome DNA by TCA when betaine was not added, as found in Example 3, was confirmed by conducting PCR in the present example.

A PCR was performed using the same *E. coli* genome DNA used in Example 3 as a template. PCR was performed using primers: forward primer (SEQ ID NO: 1) and reverse primer (SEQ ID NO: 2). This pair of primers corresponds to a region of 16S RINA. The PCR amplification was performed using a Taq polymeraze (Solgent, Korea) for 40 cycles (predenaturation at 95° C. for 1 minute, denaturation at 95° C. for 5 seconds, annealing at 60° C. for 15 seconds, and elongation at 72° C. for 15 seconds). The amplified DNA was measured using DNA 500 LABCHIP ® kit with Agilent BioAnalyzer 2100 (Agilent Technologies, Palo Alto, Calif.).

Figure 3:
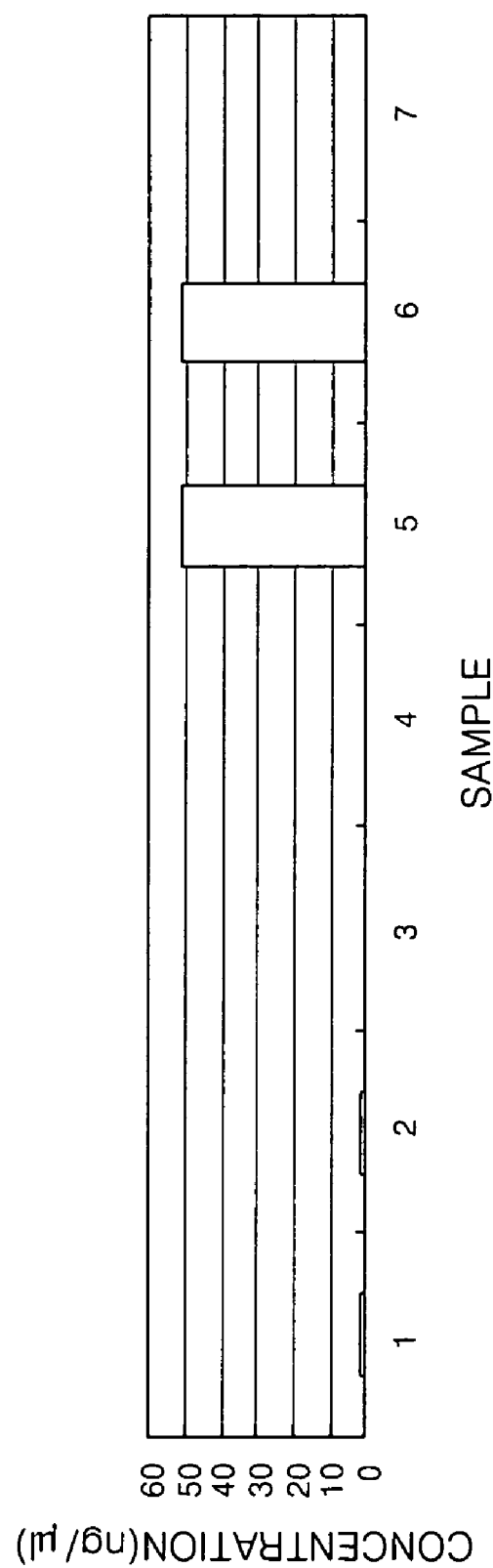
FIG. 3 is a graph of a concentration of an amplified polymerase chain reaction (PCR) product of *E. coli* genome DNA existing in a supernatant after protein was removed using TCA and polystyrene beads.

FIG. 3 is a graph of a concentration of an amplified PCR product of *E. coli* genome DNA existing in a supernatant after protein was removed using TCA and polystyrene beads. The y axis represents the concentration of the amplified DNA (ng/µl). The amount of the PCR product was quantified using Agilent BioAnalyzer 2100. Samples 1 through 4 are amplified PCR products of *E. coli* genome DNA existing in a supernatant after protein was removed using TCA and polystyrene beads. Samples 5 and 6 were used as a positive control, and prepared by performing PCR using a purified template DNA. Sample 7 was used as a negative control, and prepared conducting PCR without a template DNA. Referring to FIG. 3, it was found that when TCA and polystyrene beads were used, *E. coli* genome DNA was precipitated together with protein. As a result, DNA did not exist in the supernatant and no amplification by PCR was occured.

That is, when TCA and polystyrene beads are used to remove protein, a nucleic acid precipitates together with protein. As a result, betaine should be added together with TCA and polystyrene beads.

EXAMPLE 5

Protein Removal Effect By Betaine, TCA, and Polystyrene Beads

As determined in Example 3, betaine needs to be added to a reaction to inhibit precipitation of a nucleic acid. The present experiment was performed to determine if protein is effectively removed in the presence of betaine. The average particle diameter of polystyrene beads used was 4 µm. 0.8% TCA, 0.2 mg/ml of denatured BSA, and 0M, 0.5M or 1M betaine solution were used. First, the denatured BSA was added to each of the betaine solutions having different concentrations such that the concentration of the denatured BSA was 0.2 mg/ml. 99 µl of each of the resultant solutions was added to an Eppendorf tube and $2 \times 10^7$ particles of the polystyrene beads were added to the tube. Then, TCA was added to each of the solutions so that the final concentration of TCA was 0.8% and reacted at room temperature for 5 minutes. Subsequently, the reaction was neutralized by adding 10×PBS (Invitrogen, USA) so that a final concentration of 1×PBS was obtained. Then, the neutralized mixture was centrifuged at 5000×g for 5 minutes to precipitate the polystyrene beads, and a supernatant thereof was taken. Absorbance ($A_{280}$) of the supernatant was measured at a wavelength of 280 nm. Table 2 shows a relative amount of BSA contained in the supernatant.

TABLE 2

|  | 0M betaine | 0.5M betaine | 1M betaine |
|---|---|---|---|
| Control | 100% | 100% | 100% |
| TCA | 94.2% | 100% | 95.5% |
| TCA-Bead | 32.7% | 37.4% | 50% |

As shown in Table 2, when betaine and TCA were used, less protein was removed, but when betaine, TCA and polystyrene beads were used, more protein was removed.

Accordingly, it was found that when TCA, polystyrene beads and betaine were used, only protein could be selectively removed while a nucleic acid remained in a supernatant.

Figure 4:
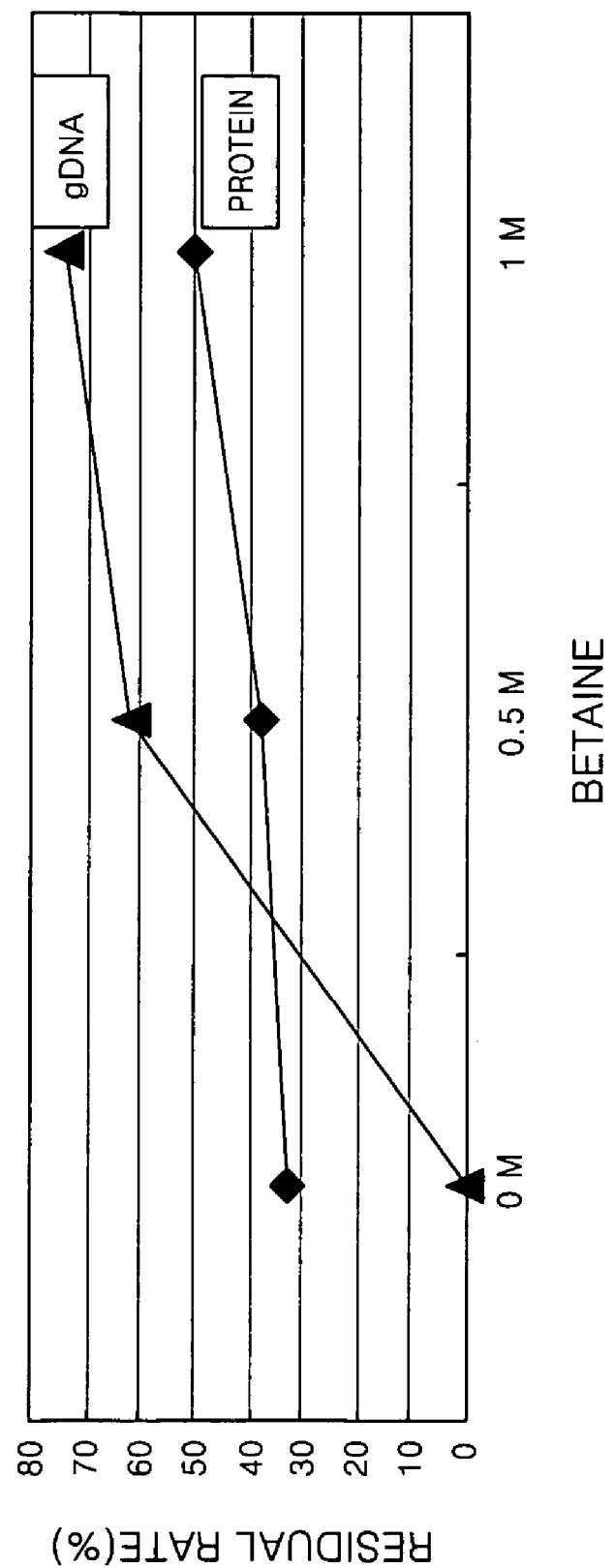
FIG. 4 is a graph of a residual rate of protein and genome DNA existing in a supernatant with respect to the concentration of betaine when a method of selectively removing protein according to an embodiment of the present invention is used.

FIG. 4 is a graph of residual rates of protein and a genome DNA contained in a supernatant with respect to the concentration of betaine when the method of selectively removing protein according to an embodiment of the present invention was used. Referring to FIG. 4, when the concentration of betaine was 0M, the entire genome DNA precipitated such that the genome DNA did not exist in the supernatant. However, when the concentration of betaine increased, the residual rate of the genome DNA in the supernatant increased. Meanwhile, when the concentration of betaine increased, the concentration of protein existing in the supernatant was also increased slightly. From these results, an optimal concentration of betaine at which more protein precipitates while a lesser amount of nucleic acid precipitates can be obtained.

EXAMPLE 6

Confirmation of Remaining Nucleic Acid with Respect to Different Concentrations of Betaine by PCR Amplification The residual rate of a nucleic acid in an *E. coli* cell lysate according to the concentration of betaine was measured through PCR amplification.

The average particle diameter of polystyrene beads used was 4 µm, and 0.8% of TCA and 0.1-1M betaine solution were used. First, betaine was added to 99 µl of *E. coli* cell lysate so that the concentration of betaine therein was 0.1 M-1M, respectively. Then TCA was added to each of the resultant solutions such that the concentration of TCA was 0.8%, and the polystyrene beads (2×107 particles) were added to the resultant solutions and reacted at room temperature for 5 minutes. Subsequently, the reaction was neutralized by adding 10×PBS (Invitrogen, USA) so that the final concentration of PBS was 1 ×PBS. PCR was performed using 10 µl of the supernatant. The PCR was performed using primers: forward primer (SEQ ID NO: 1) and reverse primer (SEQ ID NO: 2). This pair of primers corresponds to a region of 16S RINA. PCR amplification was performed using a Taq polymerase (Solgent, Korea) at 40 cycles (predenaturation at 95° C. for 1 minutes, denaturation at 95° C. for 5 seconds, annealing at 60° C. for 15 seconds, and elongation at 72° C. for 15 seconds). The amplified DNA was measured using DNA 500 LABCHIP® kit with an Agilent BioAnalyzer 2100 (Agilent Technologies, Palo Alto, Calif.).

Figure 5:
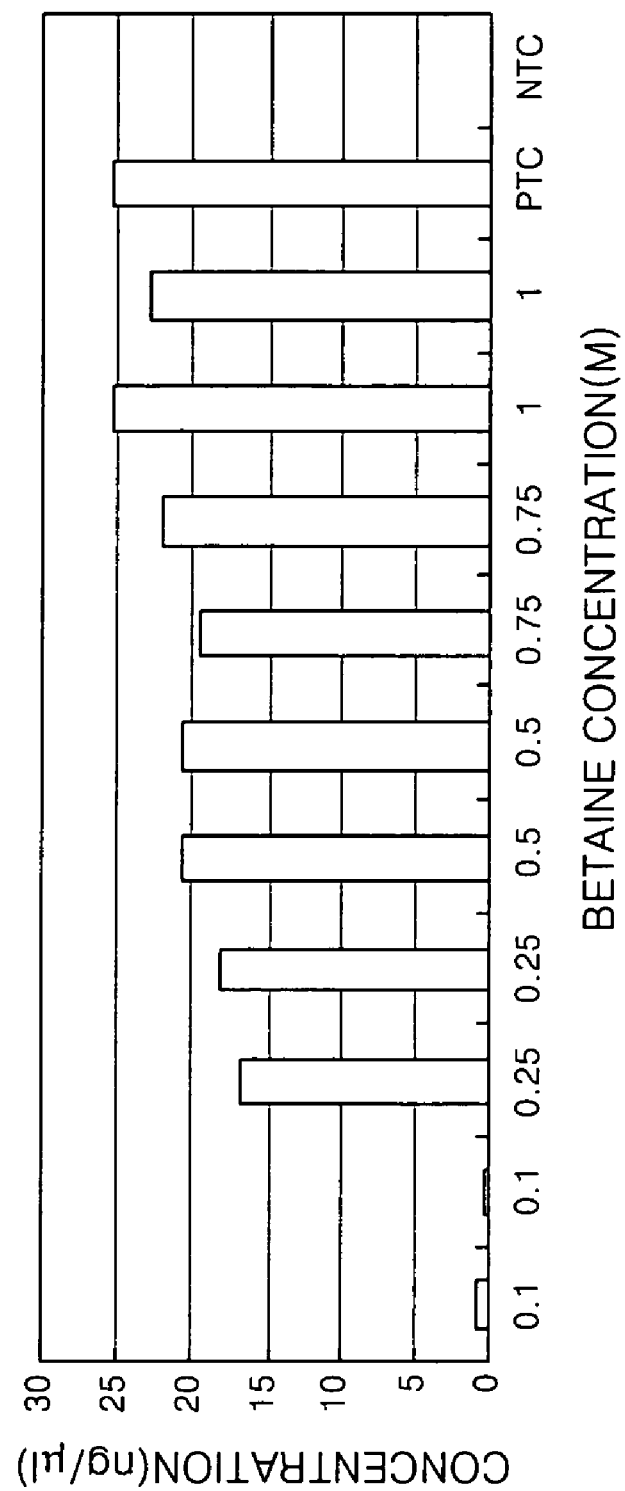
FIG. 5 is a graph of a concentration of an amplified PCR product with respect to the concentration of betaine.

FIG. 5 is a graph of a concentration of an amplified PCR product with respect to a concentration of betaine. The y axis represents the concentration of the amplified DNA (ng/µl). The amount of the PCR product was quantified using an Agilent BioAnalyzer 2100. PTC (positive control) was prepared by performing a PCR using a purified template DNA, and NTC (negative control) was prepared by performing a PCR excluding a template DNA. Referring to FIG. 5, in general, when the concentration of betaine increased, the concentration of PCR product also increased. However, when the concentration of betaine was greater than a specific value, such as 0.5M, a large difference was not found in the concentration of PCR products.

EXAMPLE 7

Effect of Compounds Having a Similar Structure to Betaine on the Inhibition of Nucleic Acid Precipitation In order to determine that a compound having a similar structure to betaine can inhibit precipitation of a nucleic acid, D-carnitine, sarcosine, and N,N-dimethylglycine having a similar structure to betaine were used. The experiment was performed in the same manner as in Example 6, except that the concentration of respective compounds used was 1M.

all of the hydrogen atoms of the amino group are substituted with methyl group was used, DNA shielding effects could be obtained to some degree. However, when sarcosine where only one hydrogen atom of the amino group is substituted with methyl group was used, DNA shielding effects could not be obtained. Accordingly, from these results, it was found that DNA protecting effects could be obtained when at least two hydrogen atoms of the amino group were substituted with an alkyl group.

As described above, proteins can be effectively removed from a biological sample containing [the] proteins and nucleic acids together while nucleic acids remain in the sample.

While the present invention has been particularly shown and described with reference to exemplary embodiments thereof, it will be understood by those of ordinary skill in the art that various changes in form and details may be made therein without departing from the spirit and scope of the present invention as defined by the following claims.

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: forward primer

<400> SEQUENCE: 1
yccakactcc tacgggaggc                                               20

<210> SEQ ID NO 2
<211> LENGTH: 22
<212> TYPE: DNA
<213> ORGANISM: Artificial Sequence
<220> FEATURE:
<223> OTHER INFORMATION: reverse primer

<400> SEQUENCE: 2
gtattaccgc rrctgctggc ac                                            22
```

Figure 6:
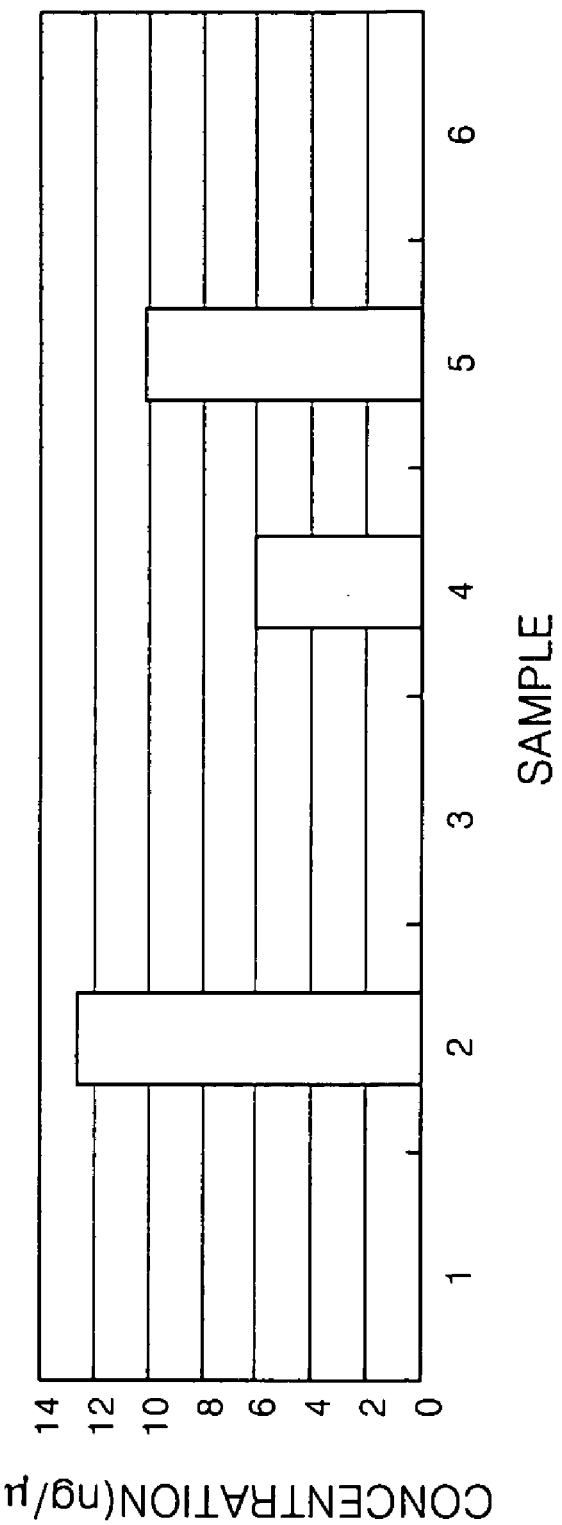
FIG. 6 is a graph of a concentration of an amplified PCR product of *E. coli* genome DNA in a supernatant after protein was removed using a compound having a similar structure to betaine.

FIG. 6 is a graph of a concentration of an amplified PCR product of *E. coli* genome DNA in a supernatant after reaction with a compound having a similar structure to betaine. The y axis represents the concentration of the amplified DNA (ng/μl). The amount of the PCR product was quantified using an Agilent BioAnalyzer 2100. Sample 1 was prepared by performing PCR using *E. coli* genome DNA in a supernatant after reaction with only TCA. Sample 2 was prepared using carnitine. Sample 3 was prepared using sarcosine. Sample 4 was prepared using N,N-dimethylglycine. Sample 5 was used as a positive control and prepared by performing PCR using a purified template DNA. Sample 6 was a negative control and prepared by performing PCR without a template DNA. Referring to FIG. 6, when only TCA was used, both *E. coli* genome DNA and protein precipitated. Therefore, since DNA did not exist in the supernatant, PCR product was not obtained. On the other hand, carnitine, which is quaternary ammonium, exhibited high DNA shielding effects and thus DNA was shielded from precipitation, and a high concentration of PCR product was obtained. When the N,N-dimethylglycine where

What is claimed is:

1. A method of selectively removing protein from a biological sample containing protein and nucleic acids, the method comprising:

adding a compound of formula I below and trichloroacetic acid (TCA) to the biological sample:

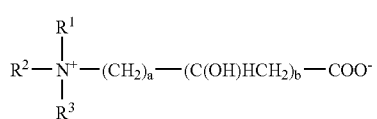

where at least two of $R^1$, $R^2$, and $R^3$ substituents are C1-C6 alkyl groups and the other substituent is a hydrogen atom or a C1-C6 alkyl group, a is an integer of 1 to 6, and b is 0 or 1, wherein b is 0 when a is not 1;

treating the resultant mixture with a hydrophobic surface material; and separating the mixture from the hydrophobic surface material to which the protein is bound.

2. The method of claim 1, wherein the compound of formula I is selected from the group consisting of betaine, carnitine, and N,N-dimethylglycine.

3. The method of claim 1, wherein a concentration of the compound of formula I is in the range of 0.15M-2M.

4. The method of claim 1, wherein a concentration of the trichioroacetic acid is in the range of 0.5% -5%.

5. The method of claim 1, wherein the hydrophobic surface material is a solid support having a hydrophobic surface, and is selected from the group consisting of a bead, a slide glass, a silicon wafer, a membrane, and a metal plane.

6. The method of claim 1, wherein the separating of the mixture from the hydrophobic surface material is performed using a method selected from the group consisting of a centrifugal method, a filtering method, and a magnetizing method.

7. The method of claim 1, wherein the separating of the mixture from the hydrophobic surface material is performed by flowing the resultant mixture through a hydrophobic material-coated microchannel of a microfluidic device.

8. The method of claim 1, wherein the mixture comprises about 60 to 74.1% of the total amount of nucleic acid present in the biological sample prior to the adding, treating, and separating.

9. The method of claim 1, wherein the mixture comprises 37.4 to 50% of the total amount of protein present in the biological sample prior to the adding, treating, and separating.

10. The method of claim 1, further comprising adding an agent selected from the group consisting of ammonium sulfate, acetone, and ethanol to the biological sample.

* * * * *